(12) United States Patent
Higham

(10) Patent No.: US 8,980,339 B1
(45) Date of Patent: Mar. 17, 2015

(54) MAMMALIAN HAIR STIMULANT AND GROWTH FORMULA

(71) Applicant: Synertek Colostrum, Inc., Cheyenne, WY (US)

(72) Inventor: Thomas E. Higham, Cheyenne, WY (US)

(73) Assignee: Synertek Colostrum, Inc., Cheyenne, WY (US)

( * ) Notice: Subject to any disclaimer, the term of this patent is extended or adjusted under 35 U.S.C. 154(b) by 0 days.

(21) Appl. No.: 14/155,989

(22) Filed: Jan. 15, 2014

Related U.S. Application Data

(60) Provisional application No. 61/754,861, filed on Jan. 21, 2013.

(51) Int. Cl.
*A01N 65/00* (2009.01)
*A61K 8/98* (2006.01)
*A61K 8/63* (2006.01)
*A61K 8/67* (2006.01)
*A61K 8/97* (2006.01)
*A61Q 7/00* (2006.01)

(52) U.S. Cl.
CPC . *A61K 8/981* (2013.01); *A61K 8/63* (2013.01); *A61K 8/678* (2013.01); *A61K 8/97* (2013.01); *A61Q 7/00* (2013.01)
USPC .......................................................... 424/725

(58) Field of Classification Search
None
See application file for complete search history.

(56) References Cited

U.S. PATENT DOCUMENTS 7,927,631 B2 4/2011 Phillips
2012/0020982 A1 1/2012 Phillips

*Primary Examiner* — Michael Meller
(74) *Attorney, Agent, or Firm* — Cochran Freund & Young LLC; James M. Weatherly

(57) ABSTRACT

Formulations for mammalian wellness including stimulating the growth and/or regrowth of mammalian hair are provided comprising colostrum and one or more of the following ingredients: lanolin, soap, such as castile soap, olive oil, chamomile oil, jojoba oil and vitamin E. Methods for the application of a formulation for stimulating the growth and/or regrowth of mammalian hair are also provided.

8 Claims, 1 Drawing Sheet

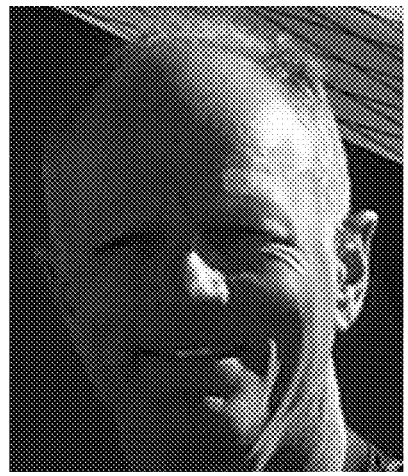
Figure 1. Photo after daily use of one 16 oz. bottle of shampoo containing the composition of the present disclosure
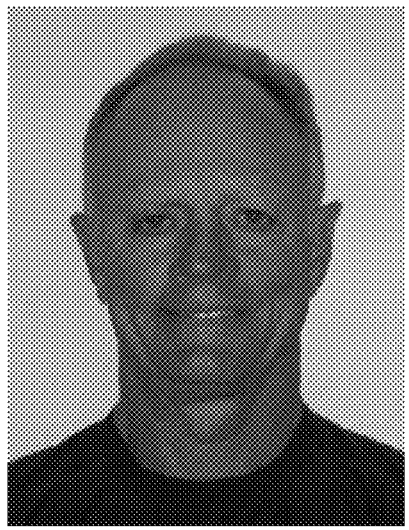
Figure 2. Photo one month after the photo of Figure 1 based on daily use of shampoo containing the composition of the present disclosure

MAMMALIAN HAIR STIMULANT AND GROWTH FORMULA

CROSS-REFERENCE TO RELATED APPLICATIONS

This application is a non-provisional patent application of and claims priority to U.S. Provisional Patent Application No. 61/754,861, filed on Jan. 21, 2013, which is herein incorporated by reference in its entirety.

BACKGROUND

Hair loss, also known as alopecia, is often defined as an excessive amount of hair loss from a mammal's skin, such as a human's scalp. Hair loss can be found in many mammals, and in particular, with humans, it can be found in both men and women of all ages. A variety of causes have been attributed to hair loss including but not limited to heredity, medications, stress and certain environmental causes.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other improvements.

An example embodiment of the present invention may comprise a composition for application to mammalian skin comprising colostrum and one or more ingredients selected from the group of lanolin, soap, including but not limited to castile soap, olive oil, chamomile oil, jojoba oil and vitamin E.

An example embodiment of the present invention may further comprise a method for promoting hair growth, comprising the steps of: providing a first composition comprising an effective amount of colostrum and one or more ingredients selected from the group of lanolin, soap, including but not limited to castile soap, olive oil, chamomile oil, jojoba oil and vitamin E and applying an effective amount of the composition to mammalian skin.

In addition to the example, aspects and embodiments described above, further aspects and embodiments will become apparent by reference to the drawings and by study of the following descriptions, any one or all of which are within the invention. The summary above is a list of example implementations, not a limiting statement of the scope of the invention.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1 is a photo of a person after daily use of one sixteen (16) ounce bottle of shampoo containing the composition of the present disclosure.

FIG. 2 is a second photo of the same person from the photo of FIG. 1, one month later after daily use of shampoo containing the composition of matter of the present disclosure.

DETAILED DESCRIPTION OF THE EMBODIMENTS

The embodiments described herein include one or more formulations for a composition of matter for mammalian wellness including but not limited to the promotion of hair growth and/or regrowth. The formulations for a composition of matter comprise colostrum and one or more ingredients comprising liquid lanolin, soap, such as castile soap, plant based oil such as olive oil, as well as chamomile oil, jojoba oil and vitamin E. The compositions of matter comprising colostrum and the one or more ingredients comprising liquid lanolin, soap, a plant based oil, chamomile oil, jojoba oil and vitamin E are thoroughly mixed together forming solutions such as but not limited to shampoo, topical liquid, paste, cream, gel or a similar substance. The composition of matter is then applied to mammalian skin, such as a human scalp in order to promote hair growth and/or hair regrowth. The composition of matter may then be applied to mammalian skin as necessary until the desired results are achieved.

The formulations for a composition of matter may also comprise multiple combinations of the preceding composition including but not limited to:

1: Colostrum, lanolin, soap, such as castile soap, a plant based oil such as olive oil, as well as chamomile oil, and jojoba oil;

2: Colostrum, lanolin, soap, such as castile soap, a plant based oil such as olive oil, as well as chamomile oil, and vitamin E;

3. Colostrum, lanolin, soap, such as castile soap, chamomile oil, vitamin E and jojoba oil;

4. Colostrum, lanolin, soap, such as castile soap, a plant based oil such as olive oil, vitamin E and jojoba oil;

5: Colostrum, lanolin, soap, such as castile soap, chamomile oil, and jojoba oil;

6: Colostrum, lanolin, soap, such as castile soap, chamomile oil, and vitamin E;

7. Colostrum, lanolin, soap, such as castile soap, a plant based oil such as olive oil as well as jojoba oil;

8. Colostrum, lanolin, soap, such as castile soap, a plant based oil such as olive oil and vitamin E;

9. Colostrum, lanolin, soap, such as castile soap, a plant based oil such as olive oil and chamomile oil;

10: Colostrum, lanolin, soap, such as castile soap, vitamin E, and jojoba oil;

11: Colostrum, lanolin, soap, such as castile soap, and jojoba oil;

12: Colostrum, lanolin, soap, such as castile soap, and vitamin E;

13: Colostrum, lanolin, soap, such as castile soap, and a plant based oil such as olive oil;

14: Colostrum, lanolin, soap, such as castile soap, and chamomile oil;

15: Colostrum, soap, such as castile soap, a plant based oil such as olive oil, as well as chamomile oil, and jojoba oil;

16: Colostrum, soap, such as castile soap, a plant based oil such as olive oil, as well as chamomile oil, and vitamin E;

17. Colostrum, soap, such as castile soap, chamomile oil, vitamin E and jojoba oil;

18. Colostrum, soap, such as castile soap, a plant based oil such as olive oil, vitamin E and jojoba oil;

19: Colostrum, soap, such as castile soap, chamomile oil, and jojoba oil;

20: Colostrum, soap, such as castile soap, chamomile oil, and vitamin E;

21. Colostrum, soap, such as castile soap, a plant based oil such as olive oil and jojoba oil;

22. Colostrum, soap, such as castile soap, a plant based oil such as olive oil and vitamin E;

23. Colostrum, soap, such as castile soap, a plant based oil such as olive oil and chamomile oil;

24: Colostrum, soap, such as castile soap, vitamin E, and jojoba oil;

25: Colostrum, soap, such as castile soap, and jojoba oil;

26: Colostrum, soap, such as castile soap, and vitamin E;

27: Colostrum, soap, such as castile soap, and a plant based oil such as olive oil; or 28: Colostrum, soap, such as castile soap, and chamomile oil.

Table 1 below shows examples of ingredients of the composition of matter and the concentrations for application of the present disclosure. Column one (1) shows a list of the ingredients of one or more embodiments of the composition of matter of the present disclosure. Column two (2) shows the weight in grams of each ingredient of one or more embodiments of the present disclosure. Column three (3) shows an example of conventional measurements of the ingredients of one or more embodiments of the present disclosure. Column four (4) shows the ingredients of one or more embodiments of the present disclosure as a percentage by weight. Column five (5) shows a range of the percentage by weight of the ingredients of one or more embodiments of the present disclosure.

TABLE 1

| Ingredient | Grams (g) | Conventional Measurements | Approximate Percentage by weight | Percentage Range By Weight |
|---|---|---|---|---|
| Colostrum | 20.0 g | 20 grams | 0.82% | 0.15% to 1.5% |
| Lanolin | 340.19 g | 12 fluid ounces | 13.96% | 13.0% to 15.0% |
| Castile Soap | 2041.17 g | 72 ounces | 83.76% | 80.0% to 86.0% |
| Jojoba oil | 5.0 g | One teaspoon | 0.21% | 0.1% to 0.3% |
| Chamomile essential oil | 0.80 g | Four drops | 0.03% | 0.005% to 0.05% |
| Vitamin E | 1.25 g | ¼ teaspoon | 0.05% | 0.01% to 0.1% |
| Olive Oil | 28.4 g | One ounce | 1.17% | 0.6% to 1.8% |

The application of the composition to mammalian skin in accordance with the teaching of the present disclosure promotes and stimulates hair growth as well as hair re-growth while also providing a mechanism for cleansing mammalian hair, as shown in FIGS. 1 and 2. For purposes of the present disclosure, the term "hair" includes but is not limited to terminal hairs and vellus hairs. Terminal hairs are often thick, long coarse hairs that are pigmented. The bulb of terminal hair follicles is often rooted deep in the skin. Vellus hairs are short, fine, hairs that tend not to have pigmentation. Vellus hairs also tend to not be rooted in the skin as compared to terminal hairs.

Mammalian hair follicles pass through three phases of a hair's life cycle, which include an anagen phase, a catagen phase and a telogen phase. The anagen phase is the active growth period of hair follicle and can last anywhere from two years to seven years. The catagen phase is a short phase at the end of the anagen phase where the hair follicle is cut off from blood supply. The catagen phase takes place over about a two to three week period and then the hair follicle transitions to the telogen phase where the hair follicle is dead.

For a healthy scalp on a mammal, it is expected that upwards of 85% to 90% of the hairs are in the anagen phase. However as hair loss begins to take place, an increasing number or percentage of the hairs enter the telogen phase Colostrum In an embodiment of the present disclosure, a composition of matter for mammalian wellness including but not limited to hair growth and/or regrowth is provided, where an aspect of the composition comprises colostrum. In mammals, including bovines, colostrum is a milky secretion from the mammary glands of mammals. Colostrum is high in antibodies and is an important source to improve the immune systems of newborns. Colostrum is also high in protein as well as vitamins and minerals.

A descriptive example of the concentration of colostrum of the composition of matter of the present disclosure contains 20 grams or making up approximately 0.82% by weight of the composition of matter described herein. However, as will be apparent to one skilled in the art, this concentration by weight may encompass any weight percentage including but not limited to a range between 0.15% by weight and 1.5% by weight and all integers in between. Therefore, while this descriptive example has 0.82% by weight, it should be understood that this description is applicable to any such concentration by weight including but not limited to weights ranging between 0.15% by weight and 1.5% by weight and all integers in between, as will be understood by one skilled in the art, once they understand the principles of this invention. In some embodiments, the term "effective amount" of colostrum may indicate an amount that is effective, when administered to stimulate the growth and/or regrowth of mammalian hair as described herein.

The preferred type of colostrum of the present disclosure is whole, powdered bovine colostrum (Synertek Colostrum, Inc., Cheyenne, Wyo.). Usually a bovine colostrum is used, harvested on average within the first six hours of parturition, although this is not to exclude colostrum in liquid form or any other state, or colostral whey, or any form of colostral whey, or any part of colostrum, or any derivative of colostrum, and also this does not exclude other forms of colostrum, including but not limited to, goat colostrum, sheep colostrum, or colostrum from any other animal.

Lanolin

Lanolin, available from Camden-Grey Essential Oils, Inc. Doral, Fla., is a substance produced by wool-bearing mammals, such as sheep. Because lanolin is a naturally produced substance, its composition can vary and may be very complex. However, generally speaking, lanolin is made up of long chain esters, as well as alcohol, acids and hydrocarbons.

By way of example of the concentration of liquid lanolin of the composition of matter of the present disclosure, 340.19 g (12 fluid ounces) of liquid lanolin is used, making up approximately 13.96% by weight of the composition of matter described herein. However, as would be obvious to one skilled in the art, this concentration by weight may encompass any weight percentage including but not limited to a range of liquid lanolin between 13.0% by weight and 15.0% by weight and all integers in between. Therefore, while this descriptive example has 13.96% by weight, it should be understood that this description is applicable to any such concentration by weight, including but not limited to weights ranging between 13.0% by weight and 15.0% by weight and all integers in between, as will be understood by one skilled in the art, once they understand the principles of this invention. In some embodiments, the term "effective amount" of lanolin may indicate an amount that is effective, when administered with colostrum as detailed herein, to stimulate the growth and/or regrowth of mammalian hair as described herein.

Surfactant

A surfactant, such as soap, is a substance that is used to lower the tension between two liquids, such as oil and water. Soap, is a surfactant, which is primarily made of oils and fats that are treated with a salt. A variety of surfactants may be used in the concentration of the present disclosure including but not limited to castile soap. Castile soap, available from Vermont Soap Organics, Middlebury, Vt., is often made from olive oil.

Eighty-three percent (83.76%) by weight, or 2041.17 g (72 fluid ounces) is an example of the concentration of surfactant or soap comprising the composition of matter of the present disclosure described herein. However, as will be discussed later, this concentration by weight may encompass any weight percentage including but not limited to a range by weight of the surfactant between 80.0% by weight and 86.0% by weight and all integers in between. Therefore, while this descriptive example has 83.76% by weight, it should be understood that this description is applicable to any such concentration by weight, including but not limited to weights ranging between 80.0% by weight and 86.0% by weight and all integers in between, as will be understood by one skilled in the art, once they understand the principles of this invention. In some embodiments, the term "effective amount" of soap may indicate an amount that is effective, when administered with colostrum as detailed herein, to stimulate the growth and/or regrowth of mammalian hair as described herein.

Jojoba Oil

Jojoba oil, Camden-Grey Essential Oils, Inc. Doral, Fla., is a liquid wax extracted from the seed of *Simmondsia chinensis* plant, which is a shrub found in the deserts of the southwestern United States and northwestern Mexico. The jojoba oil is a long chained ester.

By way of example, the concentration of jojoba oil of the present disclosure makes up 5.0 g (one teaspoon) or approximately 0.21% by weight of the composition of matter described herein. However, as will be apparent to one skilled in the art, this concentration by weight may encompass any weight percentage including but not limited to a range between 0.1% by weight and 0.3% by weight and all integers in between. Therefore, while this descriptive example has 0.21% by weight, it should be understood that this description is applicable to any such concentration by weight, including but not limited to weights ranging between 0.1% by weight and 0.3% by weight and all integers in between, as will be understood by one skilled in the art, once they understand the principles of this invention. In some embodiments, the term "effective amount" of jojoba oil may indicate an amount that is effective, when administered with colostrum as detailed herein, to stimulate the growth and/or regrowth of mammalian hair as described herein.

Plant Oil

Plant based oils are triglycerides produced or extracted from plant, often from the seeds of plants. Plant oils may include but are not limited to olive oil, extra virgin olive oil, coconut oil, soybean oil, canola oil, palm oil. Olive oil, available from Jedwards International, Quincy, Mass., is a plant-based oil produced from the pressing of the fruit of olive trees (*Olea europaea*). Olive oil is a mixture of triglyceride esters of oleic acid and palmitic acid and other fatty acids, along with other trace compounds.

An example of the concentration of olive oil of the present disclosure makes up 28.4 g (one ounce) or approximately 1.17% by weight of the composition of matter described herein. However, as will be apparent to one skilled in the art, this concentration by weight may encompass any weight percentage including but not limited to a range between 0.6% by weight and 1.8% by weight and all integers in between. Therefore, while this descriptive example has 1.17% by weight, it should be understood that this description is applicable to any such concentration by weight, including but not limited to weights ranging between 0.6% by weight and 1.8% by weight and all integers in between, as will be understood by one skilled in the art, once they understand the principles of this invention. In some embodiments, the term "effective amount" of olive oil may indicate an amount that is effective, when administered with colostrum as detailed herein, to stimulate the growth and/or regrowth of mammalian hair as described herein.

Vitamin E

There is a variety of forms of vitamin E, however vitamin E generally refers to a group of compounds called tocopherols and tocotrienols. Vitamin E compounds are often found in a variety of plants including but not limited to corn, soybeans, wheat and sunflowers. Vitamin E is an anti-oxidant but also stimulates a wide range of additional important biological functions.

A descriptive example of the concentration of vitamin E of the present disclosure, available from Camden-Grey Essential Oils, Inc. Doral, Fla., makes up 1.25 g (a ¼ teaspoon) or approximately 0.05% by weight of the composition of matter described herein. However, as will be obvious to one skilled in the art, this concentration by weight may encompass any weight percentage including but not limited to a range between 0.01% by weight and 0.1% by weight and all integers in between. Therefore, while this descriptive example has 0.05% by weight, it should be understood that this description is applicable to any such concentration by weight, including but not limited to, weights ranging between 0.01% by weight and 0.1% by weight and all integers in between, as will be understood by one skilled in the art, once they understand the principles of this invention. In some embodiments, the term "effective amount" of vitamin E may indicate an amount that is effective, when administered with colostrum as detailed herein, to stimulate the growth and/or regrowth of mammalian hair as described herein.

Chamomile Oil

Chamomile oil, including chamomile German essential oil, available from Camden-Grey Essential Oils, Inc. Doral, Fla., is an oil derived from a variety of plants from the Asteraceae family. The active ingredients of chamomile oil include but is not limited to terpene bisabolol as well as farnesene, chamazulene, flavonoids and coumarin.

An example of the concentration of chamomile oil of the present disclosure makes up 0.80 g (four drops) or approximately 0.03% by weight of the composition of matter described herein. However, as will be obvious to one skilled in the art, this concentration by weight may encompass any weight percentage, including but not limited to, a range between 0.005% by weight and 0.05% by weight and all integers in between. Therefore, while this descriptive example has 0.03% by weight, it should be understood that this description is applicable to any such concentration by weight, including but not limited to weights ranging between 0.005% by weight and 0.05% by weight and all integers in between, as will be understood by one skilled in the art, once they understand the principles of this invention. In some embodiments, the term "effective amount" of chamomile oil may indicate an amount that is effective, when administered with colostrum as detailed herein, to stimulate the growth and/or regrowth of mammalian hair as described herein.

EXAMPLES

The following examples are provided to illustrate further the various applications of the present invention and are not intended to limit the invention beyond the limitations set forth in the appended claims.

Example 1

In one embodiment described herein, a formulation is provided comprising 20.0 grams of colostrum, 340.2 grams of liquid lanolin and 2041.2 grams of castile soap. Melted, warm liquid lanolin, between 130° F. and 140° F., is added to the warm castile soap, which is also at a temperature between 130° F. and 140° F. The liquid lanolin and soap are mixed thoroughly. Twenty (20.0) grams of dried colostrum powder are then added to the lanolin and soap mixture and the three ingredients are mixed together thoroughly. The mixture is allowed to sit at room temperature for twenty-four (24) hours. After twenty-four (24) hours, the composition is again mixed thoroughly and then added a second mixture of additional castile soap at a ratio of one (1) part the first composition to three (3) parts castile soap. The first composition and the castile soap are mixed thoroughly to form the final composition. The final composition should be shaken before using as a shampoo to clean hair and to induce and promote hair growth and hair regrowth.

Example 2

In another embodiment described herein, a formulation is provided comprising 20.0 grams of colostrum, 340.19 grams of lanolin, 2041.17 grams of castile soap, and 0.80 grams of chamomile oil. As described in Example 1, the liquid lanolin is melted at a temperature between 130° F. and 140° F. and added to the warm castile soap, which is also at a temperature between 130° F. and 140° F. The lanolin and castile soap are mixed thoroughly. The chamomile essential oil is added to the lanolin and soap mixture and the three ingredients are mixed thoroughly. Finally, twenty (20.0) grams of dried colostrum powder are added to the lanolin, soap and chamomile essential oil mixture and the three ingredients are mixed together thoroughly. As with Example 1, the mixture is allowed to sit at room temperature for twenty-four (24) hours. After twenty-four (24) hours, the composition comprising colostrum is again mixed thoroughly and added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 3

In another example embodiment described herein, a formulation is provided where Example 2 is repeated, however the composition of Example 2 also includes 28.4 grams of olive oil. As described in Example 2, liquid lanolin at a temperature between 130° F. and 140° F. is added to the warm castile soap, which is also at a temperature between 130° F. and 140° F. and the lanolin and soap are mixed thoroughly. Chamomile essential oil is added to the lanolin and soap mixture and again mixed thoroughly. 28.4 grams of olive oil is added to the mixture of lanolin, castile soap and chamomile oil and all four ingredients are mixed thoroughly. Finally, twenty (20.0) grams of dried colostrum powder are added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 4

In another embodiment described herein, a formulation is provided where Example 3 is repeated, however the composition of Example 3 further includes 5.0 grams of jojoba oil. As described in Example 3, liquid lanolin, between 130° F. and 140° F., is added to the warm castile soap, which is also at a temperature between 130° F. and 140° F. The lanolin and castile soap are mixed thoroughly. Chamomile essential oil is added to the lanolin and soap mixture and the composition is mixed thoroughly. Olive oil is added to the mixture of lanolin, castile soap and chamomile oil and the four ingredients are all mixed thoroughly. The 5.0 grams of jojoba oil is then added to the mixture of lanolin, castile soap, chamomile and olive oil and the ingredients are again mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is then shaken thoroughly before using as a shampoo to clean hair and to induce and promote hair growth and hair regrowth.

Example 5

In another embodiment described herein, a formulation is provided where Example 4 is repeated, however the composition of Example 4 further includes 1.25 grams of vitamin E. As described in Example 4, liquid lanolin, between 130° F. and 140° F., is added to castile soap which is also at a temperature between 130° F. and 140° F. and the lanolin and soap are mixed thoroughly. The chamomile essential oil is added to the lanolin and soap mixture and mixed thoroughly. Olive oil is added to the mixture of lanolin, castile soap and chamomile oil and the four ingredients are also mixed thoroughly. Jojoba oil is then added to the mixture of lanolin, castile soap, chamomile and olive oil and the ingredients are again mixed thoroughly. 1.25 grams of vitamin E is added to the mixture and all six ingredients are mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 6

In another embodiment described herein, a formulation is provided comprising 20.0 grams of colostrum, 340.2 grams of liquid lanolin, 2041.2 grams of castile soap and also includes 28.4 grams of olive oil. Melted, warm liquid lanolin, between 130° F. and 140° F. is added to castile soap, which is also at a temperature between 130° F. and 140° F. The lanolin and soap are mixed thoroughly. The olive oil is added to the lanolin and soap mixture and mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 7

In another embodiment described herein a formulation is provided comprising 20.0 grams of colostrum, 340.2 grams of lanolin and 2041.2 grams of castile soap, as well as 5.0 grams of jojoba oil. Liquid lanolin, between 130° F. and 140° F., is added to castile soap, which is also at a temperature of 130° F. and 140° F. The lanolin and soap are mixed thoroughly. The jojoba oil is added to the lanolin and soap mixture and mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 8

In one embodiment described herein, a formulation is provided, comprising 20.0 grams of colostrum, 340.2 grams of lanolin and 2041.2 grams of castile soap, and further containing 1.25 grams of vitamin E. As explained above, liquid lanolin, between 130° F. and 140° F., is added to the warm castile soap, which is also at a temperature between 130° F. and 140° F. The lanolin and soap are then mixed thoroughly. Vitamin E oil is added to the lanolin and soap mixture and mixed thoroughly. Twenty (20.0) grams of dried colostrum powder are added to the mixture and the ingredients are mixed together thoroughly. Again, the mixture is allowed to sit at room temperature for twenty-four (24) hours. After twenty-four (24) hours, the composition comprising colostrum is again mixed thoroughly and added to additional castile soap at a ratio of one (1) part colostrum composition to three (3) parts castile soap. The colostrum composition and castile soap are mixed thoroughly. The mixture is then shaken thoroughly before using as a shampoo to clean hair and to induce and promote hair growth and hair regrowth.

Example 9

In one embodiment described herein a formulation is provided comprising 20.0 grams of colostrum, 340.2 grams of lanolin, 2041.2 grams of castile soap, 28.4 grams of olive oil and 5.0 grams of jojoba oil. The liquid lanolin, between 130° F. and 140° F., is added to the warm castile soap, which is also at a temperature between 130° F. and 140° F. and the lanolin and soap are mixed thoroughly. The olive oil is added to the lanolin and soap mixture and mixed thoroughly. The jojoba oil is added to the lanolin, soap and olive oil mixture and mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and added to additional castile soap at a ratio of one (1) part colostrum composition to three (3) parts castile soap. The colostrum composition and castile soap are mixed thoroughly. The mixture is then shaken thoroughly before using as a shampoo to clean hair and to induce and promote hair growth and hair regrowth.

Example 10

In one embodiment described herein a formulation is provided comprising 20.0 grams of colostrum, 340.2 grams of lanolin, 2041.2 grams of castile soap, 28.4 grams of olive oil and 1.25 grams of vitamin E. The liquid lanolin, between 130° F. and 140° F., is added to the warm castile soap, which is also at a temperature between 130° F. and 140° F. The lanolin and soap are mixed thoroughly. Olive oil is added to the lanolin and soap mixture and mixed thoroughly. Vitamin E is added and the composition is again mixed thoroughly. Finally, twenty (20.0) grams of dried colostrum powder are then added to the lanolin and soap mixture and the three ingredients are mixed together thoroughly. The mixture is allowed to sit at room temperature for twenty-four (24) hours. After twenty-four (24) hours, the composition comprising colostrum is again mixed thoroughly and then added to additional castile soap at ratio of one (1) part colostrum composition to three (3) parts castile soap. The colostrum composition and castile soap are mixed thoroughly. The mixture is then shaken thoroughly before using as a shampoo to clean hair and to induce and promote hair growth and hair regrowth.

Example 11

In another embodiment described herein, a formulation of a composition of matter is provided comprising 20.0 grams of colostrum, 340.2 grams of lanolin, 2041.2 grams of castile soap, 28.4 grams of olive oil, 5.0 grams of jojoba oil, and 1.25 grams of vitamin E. The liquid lanolin, between 130° F. and 140° F., is added to the warm castile soap, which is also at a temperature between 130° F. and 140° F. The lanolin and soap are mixed thoroughly. The olive oil is added to the lanolin and soap mixture and mixed thoroughly. Jojoba oil is added to the lanolin and soap mixture and mixed thoroughly. Vitamin E is added to the lanolin, soap, jojoba oil and olive oil mixture and the composition is mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at a ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 12

In another embodiment described herein, a formulation is provided, comprising 20.0 grams of colostrum, 340.2 grams of lanolin, 2041.2 grams of castile soap, 28.4 grams of olive oil, 5.0 grams of jojoba oil, 0.80 grams of chamomile oil and 1.25 grams of vitamin E. The liquid lanolin, between 130° F. and 140° F., is added to castile soap, which is also at a temperature between 130° F. and 140° F. The lanolin and soap are mixed thoroughly. The chamomile essential oil is added to the mixture and all three ingredients are thoroughly mixed. The olive oil is added to the lanolin, soap and chamomile essential oil mixture and mixed thoroughly. Vitamin E is added and the lanolin, soap, chamomile essential oil and olive oil composition is mixed thoroughly. The jojoba oil is added to the lanolin, soap, chamomile essential oil, olive oil and vitamin E mixture and mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four hours, the composition comprising colostrum is again mixed thoroughly and then added to additional castile soap at a ratio of one (1) part colostrum composition to three (3) parts castile soap. The colostrum composition and castile soap are mixed thoroughly. The mixture is then shaken thoroughly before using as a shampoo to clean hair and to induce and promote hair growth and hair regrowth.

Example 13

In one embodiment described herein a formulation is provided comprising twenty (20.0) grams of colostrum, twelve (12) fluid ounces of liquid lanolin, seventy-two (72) ounces of castile soap, one (1) ounce of olive oil; four (4) drop of chamomile essential oil, one (1) teaspoon of jojoba oil and one quarter (¼) teaspoon of vitamin E. Again, melted, warm liquid lanolin, between 130° F. and 140° F., is added to warm castile soap, which is also at a temperature between 130° F. and 140° F. The chamomile essential oil is added to the lanolin and soap mixture and mixed thoroughly. Olive oil is added to the mixture of lanolin, castile soap and chamomile oil and the four ingredients are also mixed thoroughly. Jojoba oil is added to the mixture of lanolin, castile soap, chamomile and olive oil and the ingredients are again mixed thoroughly. Vitamin E is added to the mixture and all the ingredients are mixed thoroughly. Finally, twenty (20.0) grams of dried colostrum powder are then added to the mixture and the ingredients are mixed together thoroughly. The mixture is allowed to sit at room temperature for twenty-four (24) hours. After twenty-four (24) hours, the composition comprising colostrum is again mixed thoroughly and then added to additional castile soap at ratio of one (1) part colostrum composition to three (3) parts castile soap. The colostrum composition and castile soap are mixed thoroughly. The mixture is shaken thoroughly before using as a shampoo to clean hair and to induce and promote hair growth and hair regrowth.

Example 14

In one embodiment described herein, a formulation is provided where any of Examples 1 through 13 are repeated, however in the embodiment described herein liquid lanolin is removed from the composition.

Example 15

In another embodiment of the present disclosure, compositions of matter consisting of colostrum and one or more ingredients consisting of liquid lanolin, soap, such as castile soap, olive oil, chamomile oil, jojoba oil and vitamin E described herein may be applied to mammalian skin. The application to mammalian skin may be conducted in a variety of manners in order to allow the composition of matter to promote hair growth and/or hair regrowth such as the composition in the form of a shampoo, topical liquid, paste, cream, gel or a similar substance.

In an example embodiment, the composition of matter is used in the form of a shampoo. The shampoo is applied daily to the scalp of a human. Water is added to the shampoo and the composition is brought to a lather. The composition is then rinsed thoroughly from the scalp. This process is then repeated daily.

FIG. 1 is a photo of a person after daily use of one 16-ounce bottle of shampoo containing the composition of matter of the present disclosure as discussed in Examples 1 to 15. FIG. 2, is a second photo of the same person one month later after daily use of shampoo containing the composition of matter of the present disclosure. As shown in FIG. 2, hair growth and regrowth is visible on the scalp of the individual in the photo. Additional hair can be seen in the upper right portion of the person's scalp of FIG. 2 when compared with the same area of the scalp as shown in FIG. 1.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A composition consisting essentially of jojoba oil, colostrum, chamomile oil, lanolin, vitamin e.

2. A composition consisting essentially of jojoba oil, olive oil, colostrum, chamomile oil, lanolin, vitamin e.

3. A soap consisting essentially of jojoba oil, olive oil, colostrum, chamomile oil, lanolin, vitamin e.

4. A soap consisting essentially of jojoba oil, colostrum, chamomile oil, lanolin, vitamin e.

5. A method for promoting hair growth consisting essentially of applying a therapeutically effective amount of a composition consisting essentially of jojoba oil, colostrum, chamomile oil, lanolin, vitamin e to mammalian skin.

6. A method for promoting hair growth consisting essentially of applying a therapeutically effective amount of a soap consisting essentially of jojoba oil, colostrum, chamomile oil, lanolin, vitamin e to mammalian skin.

7. A method for promoting hair growth consisting essentially of applying a therapeutically effective amount of a soap consisting essentially of jojoba oil, olive oil, colostrum, chamomile oil, lanolin, vitamin e to mammalian skin.

8. A method for promoting hair growth consisting essentially of applying a therapeutically effective amount of a composition consisting essentially of jojoba oil, colostrum, olive oil, chamomile oil, lanolin, vitamin e to mammalian skin.

* * * * *